US007846875B2

(12) United States Patent
Hoang et al.

(10) Patent No.: US 7,846,875 B2
(45) Date of Patent: Dec. 7, 2010

(54) COUPLING AGENTS COMPRISING A PHOTOLABILE PROTECTING GROUP AND USES THEREOF, SUCH AS FOR THE FUNCTIONALISATION OF SOLID SUPPORTS

(75) Inventors: Antoine Hoang, Grenoble (FR); Françoise Vinet, Grenoble (FR); Eric Defrancq, Saint-Pierre-D'Allevard (FR); Pascal Dumy, Allevard (FR)

(73) Assignees: Commissariat A l 'Energie Atomique, Paris (FR); Universite Joseph Fourier, Grenoble Cedex (FR)

( * ) Notice: Subject to any disclaimer, the term of this patent is extended or adjusted under 35 U.S.C. 154(b) by 704 days.

(21) Appl. No.: 11/572,668

(22) PCT Filed: Jul. 11, 2005

(86) PCT No.: PCT/FR2005/001786

§ 371 (c)(1), (2), (4) Date: Aug. 3, 2007

(87) PCT Pub. No.: WO2006/024722

PCT Pub. Date: Mar. 9, 2006

(65) Prior Publication Data

US 2007/0298516 A1 Dec. 27, 2007

(30) Foreign Application Priority Data

Jul. 28, 2004 (FR) .................................. 04 08318

(51) Int. Cl.
*C04B 50/18* (2006.01)

(52) U.S. Cl. .............................. 506/32; 506/3; 548/542

(58) Field of Classification Search ....................... None
See application file for complete search history.

(56) References Cited

U.S. PATENT DOCUMENTS 6,686,461 B1 * 2/2004 Schwartz et al. ......... 536/26.26
6,965,040 B1 * 11/2005 Gao et al. ................... 549/439

FOREIGN PATENT DOCUMENTS

WO WO 97/39151 A 10/1997

OTHER PUBLICATIONS

Podyminogin et al (2001 Nucleic Acids Research 29:5090-5098).*
Bhushan K.R. et al., "Synthesis of photoliable 2-(2-nitrophenyl)propyloxycarbonyl protected amino acids", *Tetrahedron Letters*, Elsevier Science Publishers, vol. 44, No. 47, Nov. 17, 2003, pp. 8585-8588.
Acedo M. et al., "N-2-(2,4-dinitrophenyl)ethyloxycarbonyl-Amino Acids, New Base Labile Protected Derivatives Suitable for Solid-Phase Peptide Synthesis", *Tetrahedron Letters*, vol. 33, No. 34, 1992, pp. 4989-4992.

* cited by examiner

*Primary Examiner*—Christopher Low
*Assistant Examiner*—Christopher M Gross
(74) *Attorney, Agent, or Firm*—Alston & Bird LLP

(57) ABSTRACT

The invention relates to compounds comprising a photolabile protecting group and to the use thereof as coupling agents for the functionalisation of solid supports. The invention also relates to the solid supports functionalised by said compounds and to the use of same for the immobilisation of biological molecules of interest, such as nucleic acid molecules.

17 Claims, 1 Drawing Sheet

COUPLING AGENTS COMPRISING A PHOTOLABILE PROTECTING GROUP AND USES THEREOF, SUCH AS FOR THE FUNCTIONALISATION OF SOLID SUPPORTS

CROSS-REFERENCE TO RELATED APPLICATIONS

This is a national phase application under 35 U.S.C. 371 of International Application No. PCT/FR2005/001786 filed Jul. 11, 2005, which claims priority from French application No. 0408318 filed Jul. 28, 2004.

FIELD AND BACKGROUND OF THE INVENTION

The present invention relates to coupling agents comprising a photolabile protecting group and to the use thereof for the functionalization of solid supports. The present invention also relates to the solid supports functionalized with these coupling agents, and also to the use thereof for the immobilization of biological molecules of interest, in particular of nucleic acid molecules.

Various methods for the covalent grafting of biological molecules of interest, and in particular of nucleic acid such as oligonucleotides (ON), onto a solid support have already been proposed. In the specific context of the attachment of ONs, these methods can be divided into two main categories:

1) In situ synthesis, which consists in constructing the ON molecule step by step on a solid support using the principle of synthesis via the phosphoramidite pathway. This method, described in particular in international application WO 97/39151, allows the preparation of surfaces with a high density of ONs. In addition, by means of a set of blanking plates and the use of photolabile protecting groups, it allows the targeting of the various ONs on the support. However, this method has a certain number of major disadvantages. In particular, the ONs attached to the support cannot be characterized and it is very difficult to incorporate ONs carrying modifications.

2) Synthesis by deposition, or ex situ, which consists, firstly, in preparing the ON conventionally and then, secondly, in attaching it to a solid support using a suitable chemical reaction. This second method has in particular the advantage of using ON molecules that can be characterized before they are attached to the solid support.

The invention which will be described hereinafter falls more especially within the context of methods of synthesis by deposition.

Several types of methods of synthesis by deposition have already been described in the prior art, in particular as regards the various techniques for localizing the grafting of the ON.

Mention may, firstly, be made of methods using the electrochemical pathway, which consist in anchoring the ON, functionalized beforehand with an electrically conducting group, for instance a pyrrole group, via electropolymerization of the pyrrole residue. This type of electrochemical ON deposition method has in particular been described in patent FR 2 703 359. It nevertheless has the drawback of requiring the use of an electrically conducting support, which makes the final component complex. Furthermore, in a component of “Lab on a Chip” type, the various fabrication steps can impair the quality of the electrodes and therefore their functionality.

Mention may, secondly, be made of the photochemical pathway, which appears to be more promising since the management of the surfaces and of the chemical solutions to be used is externalized. Two approaches have been developed:

i) direct photografting between the surface and the target molecule. In this case, the photografting has the disadvantage of involving free-radical reactions which are not very selective;

ii) the freeing of a function protected with a photolabile protecting group on the support, so as to allow subsequent reaction with the target ON in order to produce attachment thereof. In this case, the supports used are generally functionalized with coupling agents which are bifunctional compounds comprising, at one of their ends, a function for attachment to the surface of the support and, at the other end, a function that is reactive with respect to a target molecule comprising a complementary chemical function, said reactive function of the coupling agent being protected with a photolabile group. However, in order to be competitive, the latter approach must satisfy a certain number of criteria. These criteria are the following:

- the reaction between the activated support and the target molecule must be rapid; this reaction can only occur when the reactive functions of the coupling agent have been freed from their protecting group (activation reaction);
- the yield from this reaction must be high;
- the method of synthesis for preparing the coupling agents must be simple to carry out and comprise as few steps as possible;
- the use of mild reaction conditions (water, for example);
- the bond formed between the coupling agent and the target molecule must be stable under various conditions of temperature and pH so as to allow very flexible use of the support thus functionalized.

Now, it appears that the various methods proposed to date do not satisfy all these criteria entirely satisfactorily, in particular due to the nature of the various coupling agents used.

SUMMARY OF THE INVENTION

For this reason, the inventors have given themselves the aim of providing novel bifunctional coupling agents comprising a reactive function protected with a photolabile group, which are easy to synthesize, according to a process comprising few steps and which can be carried out under mild conditions, it being possible for these coupling agents to be advantageously used for functionalizing solid supports with the aim of subsequently attaching target biological molecules thereto.

A first subject of the present invention is thus a coupling agent of formula (I) below:

A—X—B—Proc (I)

in which:

- A represents a function for attachment to a solid support, said function being chosen from functions of amine, phosphoramidite, silane and activated ester type;
- X represents a spacer arm;
- B is a reactive function chosen from groups that result, after photodeprotection, in a function of the type oxyamine (—$ONH_2$) and derivatives or hydrazide (—NH—$NH_2$) and derivatives, said function B being protected with a Proc group;

Proc is a photolabile protecting group of formula (II) below:

(II)

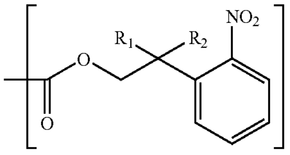

in which:

$R_1$ and $R_2$, which may be identical or different, represent a hydrogen atom or a $C_1$-$C_4$ alkyl radical.

According to the invention, the function A will be chosen according to the nature of the support to which the coupling agents of formula (I) will be intended to be attached. The functions of activated ester type are preferably carboxylic acid functions esterified with N-hydroxysuccinimide, or else with any other suitable activation reagent known to those skilled in the art, for instance pentafluorobenzene.

The spacer arm X may vary in length and in polarity according to the desired final properties. It may, for example, be an uncharged hydrophobic chain (such as a saturated hydrocarbon-based chain) or else an uncharged hydrophilic chain such as a glycol ether.

According to a particularly preferred embodiment of the invention, the spacer arm X is chosen from saturated hydrocarbon-based chains containing from 1 to 13 carbon atoms, and glycol ethers in which the carbon-based chain contains from 4 to 12 carbon atoms, such as triethylene glycol (TEG) and hexaethylene glycol (HEG).

The reactive function B is a function which allows, after photodeprotection, the covalent attachment of target molecules carrying at least one complementary chemical function. These reactive functions B will be capable of interacting with a complementary function carried by said target molecules, such as amine functions, alcohols, thiols, carboxyls or carbonyls. A more exhaustive list of the pairs of complementary functional groups can be easily found in any organic chemistry monograph.

Within the protecting groups of formula (II) above, and when they represent an alkyl radical, $R_1$ and $R_2$, independently of one another, are preferably chosen from methyl and ethyl radicals; the methyl radical being most particularly preferred.

Among the coupling agents of formula (I) above, preference is particularly given to those in which:

i) A represents a phosphoramidite function,
 X represents a saturated hydrocarbon-based chain having 6 carbon atoms,
 B represents an oxyamine function (—ONH—), and
 $R_1$ and $R_2$ represent a hydrogen atom or a methyl radical;

ii) A represents a tri($C_1$-$C_4$) alkoxysilane,
 X represents a saturated hydrocarbon-based chain having from 2 to 12 carbon atoms,
 B represents an oxyamine function (—ONH—), and
 $R_1$ and $R_2$ represent a hydrogen atom or a methyl radical;

iii) A represents a carboxylic function esterified with N-hydroxysuccinimide, or pentafluorobenzene,
 X represents —$CH_2$—,
 B represents an oxyamine function (—ONH—), and
 $R_1$ and $R_2$ represent a hydrogen atom or a methyl radical.

Among the compounds defined in point iii) above, preference is most particularly given to the compounds in which the function A is triethoxysilane and X is a saturated hydrocarbon-based chain having 3 or 11 carbon atoms. The coupling agents of formula (I) above can be readily prepared according to the principles of organic synthesis well known to those skilled in the art and depending on the nature of the functions A and B.

According to a first embodiment of the invention, and when the coupling agent is a compound of formula (I) in which the attachment function A is of the type of a carboxylic acid activated in the form of an N-hydroxysuccinimide ester, for example, and the function B is an oxyamine function, a preparation process corresponding to scheme 1 below is preferably used:

SCHEME 1

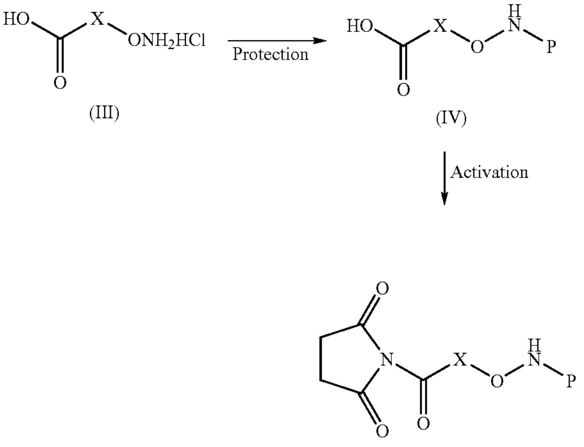

(III) (IV) (I)

In this scheme, Proc is a photolabile protecting group of formula (II) as defined above and X is a spacer arm that can have the same meanings as those indicated above.

According to this scheme, a compound of formula (III) comprising a carboxylic function and an oxyamine function is, in a first step, protected with a Proc photolabile protecting group of chosen formula (II), so as to produce a compound of formula (IV), and then, in a second step, the carboxylic acid function of the compound of formula (IV) is activated with N-hydroxysuccinimide, so as to produce the expected compound of formula (I).

According to a second embodiment of the invention, and when the coupling agent is a compound of formula (I) in which the attachment function A is a phosphoramidite function and the function B is an oxyamine function, a preparation process corresponding to scheme 2 below is preferably used:

SCHEME 2

SCHEMA 2

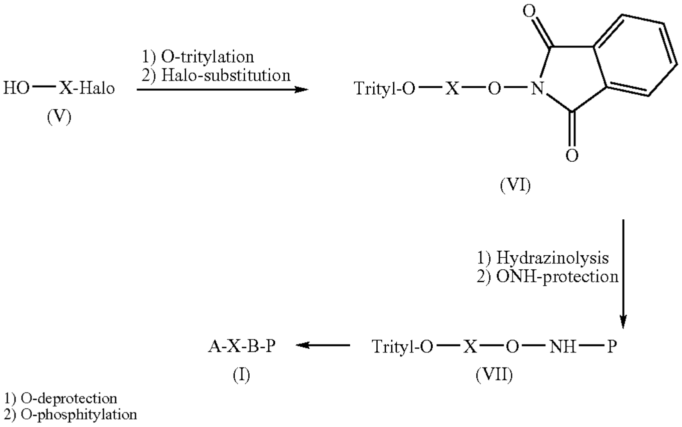

(V) (VI) (VII) (I)

On this scheme, X and Proc have the same meanings as those indicated above, B represents an oxyamine function and A denotes the following group:

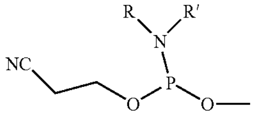

in which R and R', which may be identical or different, represent an alkyl radical having from 1 to 13 carbon atoms.

According to this scheme, in a first step, a halogenated alcohol of formula (V) in which Halo represents a halogen atom, such as bromine, chlorine, iodine or fluorine, is reacted with N-hydroxyphthalimide (nucleophilic substitution of the halogen atom) so as to obtain a compound of formula (VI) which, in a second step, undergoes a hydrazinolysis in order to free the oxyamine function which is subsequently protected with a photolabile Proc protecting group of chosen formula (II) so as to produce a compound of formula (VII) which, in a third step, undergoes a phosphitylation so as to produce the expected compound of formula (I).

According to a third embodiment of the invention, and when the coupling agent is a compound of formula (I) in which the attachment function A is of silane type and the function B is an oxyamine function, a preparation process corresponding to scheme 3 below is preferably used:

SCHEME 3

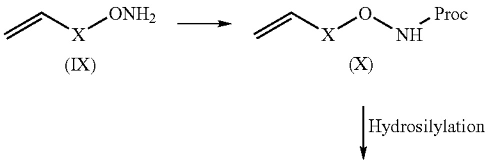

(IX) (X)

-continued

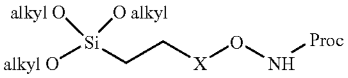

(I)

According to this process, the oxyamine function of an alkene compound of formula (IX) in which X represents a spacer arm that can have the same meanings as those indicated above for the coupling agents of formula (I), is protected, so as to obtain a compound of formula (X) which subsequently undergoes a hydrosilylation so as to produce a compound of formula (I) in which the attachment function A is a tri($C_1$-$C_4$)alkoxysilane function.

The coupling agents of formula (I) in accordance with the invention can be used for the functionalization of solid supports. A subject of the present invention is therefore the use of at least one coupling agent of formula (I) as defined above, for the functionalization of solid supports.

The use of the coupling agents of formula (I) advantageously makes it possible to rapidly modify the surface of solid supports with a stable layer carrying reactive functions that are readily accessible by photodeprotection.

Thus, a subject of the present invention is also a process for preparing a functionalized solid support, characterized in that it comprises at least one step of bringing at least one surface of a solid support into contact with a solution of at least one coupling agent of formula (I) in an organic solvent.

The organic solvent is preferably chosen from nonpolar solvents such as, for example, trichloroethylene, dimethylformamide (DMF) and cyclohexane.

The bringing into contact of the solid support with the solution of the coupling agent of formula (I) is preferably carried out at a temperature of between approximately 4 and 80° C., for approximately 1 to 48 hours.

The substrate is subsequently rinsed with one or more solvents, preferably and successively with the reaction solvent, absolute ethanol and/or chloroform, and then dried, preferably with nitrogen.

This process has the advantage of being simple to carry out and makes it possible to obtain a layer of good density. It makes it possible in particular to obtain solid supports comprising at least one surface functionalized with a self-assembled monolayer (SAM) of compounds of formula (I). SAMs are defined as an assembly of molecules in which the molecules are organized, which organization is due to interactions between the chains of the molecules, giving rise to a stable, monomolecular and ordered anisotropic film (A. ULMAN, Chem. Rev., 1996, 96, 1533-1554). It is in particular possible to obtain such SAMs when the surface of a solid support is functionalized with a coupling agent of formula (I) in accordance with the invention in which the attachment function A is a function of silane type, preferably in solution at approximately 10 mM in a solvent such as trichloroethylene, and when the bringing into contact is carried out at a temperature of approximately 4° C. for approximately 24 hours.

Moreover, the surfaces obtained by carrying out the process in accordance with the invention exhibit, directly, a large number of reactive functions protected with a photolabile protecting group that is easy to remove selectively in time and space in order to covalently immobilize biological molecules of interest comprising a chemical function that is complementary with respect to the reactive function B of the coupling agents present at the surface of the solid support.

The solid supports that may be functionalized with the coupling agents of formula (I) in accordance with the invention are preferably chosen from supports made of glass, ceramics (of oxide type), silicon or plastic, said supports comprising at least one hydrated, hydroxylated, silanized or aminated surface or alternatively a surface of activated ester type. Such surfaces can be readily prepared according to well-known techniques of the prior art. It is, for example, possible to prepare a solid support comprising a hydroxylated surface by silanization by means of a silane epoxide which subsequently undergoes acid hydrolysis so as to free the hydroxyl functions of the surface.

These solid supports have at least one planar or nonplanar, smooth or structured surface and may, for example, be in the form of a glass slide, a planar plastic plate or a plastic plate with wells, a capillary tube or else a porous or nonporous bead.

As described above, the attachment function A of the coupling agents of formula (I) is chosen according to the nature of the surface of the support to which said coupling agents are intended to be attached.

Thus, when they are supports comprising at least one surface of activated ester type, then the function A is preferably an amine function; when they are supports comprising at least one surface of hydroxyl type, then the function A is preferably a phosphoramidite or silane function; when they are supports comprising at least one surface of hydride type, then the function A is preferably a silane function and when they are supports comprising an aminated surface, then the function A is preferably an activated ester function.

A subject of the present invention is therefore also the solid supports comprising at least one surface functionalized with one or more coupling agents of formula (I) as defined above.

Such supports can advantageously be used for the immobilization of biological molecules of interest comprising a chemical function that is complementary with respect to the reactive function B of the coupling agents of formula (I) present at the surface of said solid support after they have been deprotected, and in particular for the covalent immobilization of nucleic acid molecules such as DNA and oligonucleotides.

Thus, a subject of the present invention is also the use of a solid support as described above, for the covalent immobilization of biological molecules of interest comprising a chemical function that is complementary with respect to the reactive function B of the coupling agents of formula (I) present at the surface of said solid support, and in particular of nucleic acids (DNA, oligonucleotides), through the formation of an amide bond (peptide).

A subject of the present invention is also a process for immobilizing biological molecules of interest, and in particular nucleic acid molecules, on a solid support as described above, characterized in that it comprises at least a first step of photo-deprotection of the reactive functions B of the compounds of formula (I) by exposure of at least a part of the surface of the solid support, followed by bringing the solid support thus activated into contact with a solution of biological molecules of interest, and in particular of nucleic acid molecules, so as to result in the immobilization of said molecules through the formation of a covalent bond between at least one chemical function that is carried by said molecules and that is reactive with respect to the reactive functions B of said compounds of formula (I) in accordance with the invention, on said solid support, and the optional repetition of these two steps.

In particular, the photo-deprotection step may be localized on only a part of the functionalized surface of the solid support and, for example, carried out through a mask.

After exposure, the reactive function B of the coupling agents of formula (I) is in a deprotected (active) state, which thus creates zones carrying the free reactive function which may capture any molecule in solution comprising a chemical function that is reactive with respect to said activated reactive function B present at the surface of the solid support.

In particular, the immobilization step is carried out through the formation of oxime bonds between the oxyamine functions B of the compounds of formula (I) and the carbonylated functions of the biological molecules of interest, in particular of the nucleic acid molecules. This reaction has the advantage of being able to be carried out under mild conditions, in particular at a pH of between 4 and 7. The bond formed (oxime) exhibits, moreover, a great stability and it is not necessary to stabilize it by means of an additional reduction step.

The exposure wavelength is preferably between 300 and 400 nm.

The solutions of biological molecules of interest may be simple aqueous solutions or else solutions of these molecules in buffered aqueous solutions.

The duration of the bringing into contact is preferably between approximately 5 and 60 minutes and is carried out at a temperature preferably of between approximately 4 and 60° C.

Finally, a subject of the invention is also the solid supports (nucleic acid chips, in particular) as described above and obtained by carrying out the immobilization process in accordance with the invention, i.e. comprising at least one surface on which said biological molecules of interest, and in particular nucleic acid molecules, are immobilized by means of a covalent bond formed with the reactive function B of the coupling agents of formula (I) in accordance with the invention.

BRIEF DESCRIPTION OF THE DRAWINGS

Besides the above arrangements, the invention also comprises other arrangements that will emerge from the following description, which refers to examples of preparation of coupling agents of formula (I), to examples of functionalization of glass solid supports of capillary tube type or planar solid supports with coupling agents of formula (I) in accordance with the invention, to the use of these functionalized supports for the immobilization of oligonucleotides, and also to the attached FIGS. 1 and 2 in which.

DETAILED DESCRIPTION

Example 1

Figure 1:
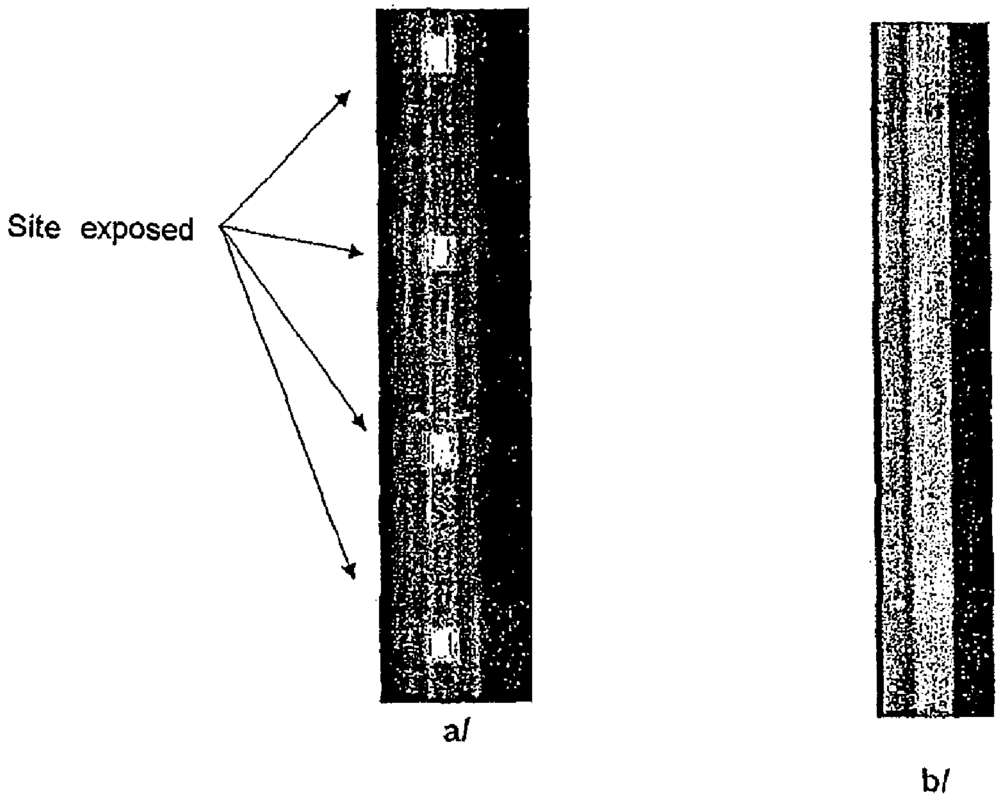
FIG. 1 represents the photograph of the fluorescence emitted by oligonucleotides attached to a solid support of capillary tube type according to the process in accordance with the invention, after hybridization with complementary oligonucleotides labeled with a fluorophore (capillary tube of type a/), compared with a nonfunctionalized capillary tube (capillary tube of type b/)

Preparation of a Phosphoramidite Derivative in Accordance with Formula (I)

(6)

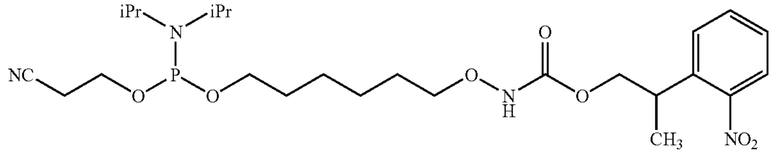

1) First step: Preparation of compound (1): introduction of the oxyamine (1)

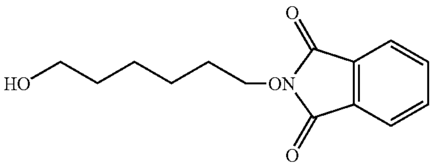

A solution of N-hydroxyphthalimide (2.70 g; 16.6 mmol) and of potassium carbonate (4.6 g; 23.6 mmol) in 150 ml of dimethylformamide (DMF) was heated at a temperature of 50° C. under argon for one hour with stirring. 6-Bromohexanol (3 g; 16.6 mmol) was subsequently added, and then the reaction mixture was again stirred overnight at a temperature of 50° C. After filtration, the solvent was evaporated off under reduced pressure. 50 ml of ethyl acetate were subsequently added to the residue thus obtained and then the organic phase was washed with 0.1 N sodium hydroxide and then with a saturated aqueous solution of sodium chloride. The organic phase was subsequently dried over anhydrous sodium sulfate and then evaporated. The product (1) was obtained in the form of a white powder (3.28 g; 12.5 mmol; yield 75%) having a melting point of between 85 and 88° C.

The proton nuclear magnetic resonance ($^1H$-NMR) analysis, carried out at a wavelength of 200 MHz in $CDCl_3$, was as follows: δ ppm=1.30-1.90 (8H, m, $4C\underline{H}_2$), 3.60 (2H, t, J=13 Hz, $C\underline{H}_2O$), 4.20 (2H, t, J=13 Hz, $C\underline{H}_2ON$), 7.70-7.90 (4H, m, Ar—H).

MS (DCI, positive mode): $M_{calc}$–263 ($C_{14}H_{17}NO_4$), m/z=281 $[M+NH_4]^+$.

2) Second Step: Tritylation of Compound (1) so as to Produce the Compound (2)

(2)

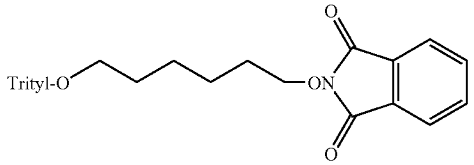

Trityl chloride (4.2 g; 15 mmol) was added to a solution of compound (1) obtained above in the preceding step (3.2 g; 12.5 mmol) in 75 ml of anhydrous pyridine. The solution was stirred under argon overnight at ambient temperature. 5 ml of methanol were subsequently added slowly, and then the solvent was evaporated off under reduced pressure. The residue obtained was then solubilized in 100 ml of ethyl acetate and the organic phase was then washed with water and then with a saturated aqueous solution of sodium chloride. The organic phase was then dried over anhydrous sodium sulfate and then evaporated. The crude product was purified by silica gel chromatography (eluent dichloromethane/cyclohexane: 75/25, v/v). The product (2) was obtained in the form of a white powder (6.27 g, 12.4 mmol; yield 99%) that melts at 106-107° C.

The $^1H$-NMR analysis (200 MHz, $CDCl_3$) was as follows: δppm=1.30-1.90 (8H, m, 4 $C\underline{H}_2$), 3.20 (2H, t, J=13 Hz, $C\underline{H}_2O$), 4.20 (2H, t, J=13 Hz, $C\underline{H}_2ON$), 7.70-7.90 ($4H_{Ar}$, m, Ar—$\underline{H}$-phthalimide), 7.20-7.40 (15H, m, Ar—$\underline{H}$-trityl).

MS (ESI, positive mode): $M_{Calc}$=505 ($C_{33}H_{31}NO_4$), m/z=528 $[M+Na]^+$, m/z=544 $[M+K]^+$.

3) Third Step: Hydrazinolysis of Compound (2) so as to Obtain Compound (3)

(3)

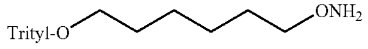

Compound (2) obtained above in the second step (6.27 g; 12.4 mmol) were solubilized in 50 ml of dichloromethane and 780 mg of hydrazine (24.8 mmol) were added. The solution obtained was brought to reflux for 1 and a half hours and then filtered and evaporated under reduced pressure. The crude product was purified by silica gel chromatography, with the eluent being dichloromethane and then a 95/5 (v/v) mixture of dichloromethane and methanol. Compound (3) was obtained in the form of an oil (4.20 g; 11.2 mmol) with a yield of 90%.

$^1$H-NMR (200 MHz, $CDCl_3$): δ ppm=1.30-1.80 (8H, m, 4 $C\underline{H}_2$), 3.10 (2H, t, J=13 Hz, $C\underline{H}_2$O-Tri), 3.60 (2H, t, J=13 Hz, $C\underline{H}_2$ON), 7.70-7.90 (15H, m, Ar—$\underline{H}$-trityl).

MS (ESI, positive mode): $M_{calc}$=375 ($C_{25}H_{29}NO_2$), m/z=376 $[M+H]^+$, m/z=398 $[M+Na]^+$, m/z=414 $[M+K]^+$.

4) Fourth Step: Protection of the Oxyamine of Compound (3) so as to Obtain Compound (4)

(4)

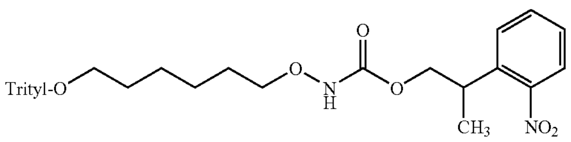

Compound (3) prepared above in step 3 (4.20 g; 11.2 mmol) was dissolved in 100 ml of pyridine. 50 ml of a solution of dichloromethane containing 5.40 g (22.4 mmol) of 2-(2-nitrophenyl)propyl chloroformate (Cl—NPPOC) were subsequently added dropwise. The reaction mixture was stirred for one hour in the dark and then evaporated under reduced pressure. The residue obtained was subsequently solubilized in dichloromethane and then the organic phase was washed with a saturated aqueous solution of sodium chloride. The organic phase was dried over anhydrous sodium sulfate and then evaporated. The crude product was purified by silica gel chromatography using dichloromethane as eluent. The product (4) was obtained in the form of an orange oil (5.80 g; 9.9 mmol) with a yield of 89%.

$^1$H-NMR (200 MHz, $CDCl_3$): δ ppm=1.30 (3H, d, J=16 Hz, $C\underline{H}_3$), 1.50-1.80 (8H, m, 4 $C\underline{H}_2$), 3.0 (2H, t, J=13 Hz, $C\underline{H}_2$O-Tri), 3.70 (2H, m, $C\underline{H}_2$ON, 1H, m C$\underline{H}$), 4.20 (2H, t, J=13 Hz, $C\underline{H}_2$OCO), 7.10-7.50 (15H, m, Ar—$\underline{H}$-trityl), 7.50-7.80 (4H, m, Ar—$\underline{H}$ NPPOC).

MS (ESI, positive mode): $M_{calc}$=582 ($C_{35}H_{38}N_2O_6$), m/z=605 $[M+Na]^+$, m/z=621 $[M+K]^+$.

MS (ESI, negative mode): m/z=581 $[M-H]^-$.

5) Detritylation of Compound (4) so as to Obtain Compound (5)

(5)

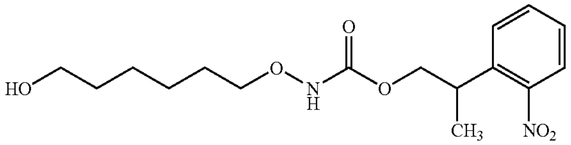

5.80 g (9.90 mmol) of compound (4) obtained above in the preceding step were dissolved in 50 ml of a solution of trifluoroacetic acid at 20% in dichloromethane. The mixture was stirred for 3 to 4 hours at ambient temperature and then evaporated under reduced pressure. The residue obtained was solubilized in 100 ml of dichloromethane and then the organic phase was washed with a saturated aqueous solution of NaCl. The organic phase was then dried over anhydrous sodium sulfate and then evaporated. The crude product was purified by silica gel chromatography using dichloromethane and then a 95/5 (v/v) dichloromethane/methanol mixture as eluent. Compound (5) was obtained in the form of an orange oil (3.0 g; 8.9 mmol) with a 90% yield.

$^1$H-NMR (200 MHz, $CDCl_3$): δ ppm=1.30 (3H, d, J=16 Hz, $C\underline{H}_3$), 1.50-1.80 (8H, m, 4 $C\underline{H}_2$), 3.70 (2H, m, $C\underline{H}_2$ON, 1H, m, C$\underline{H}$), 4.30 (2H, t, $C\underline{H}_2$OCO, 2H, t, $C\underline{H}_2$OH), 7.50-7.80 (4H, m, Ar—$\underline{H}$ NPPOC).

MS (DVI, positive mode): $M_{calc}$=340 ($C_{16}H_{24}N_2O_6$), m/z=454 $[M+TFA]^+$.

6) Sixth Step: Phosphitylation of Compound (5) so as to Produce Compound (6)

(6)

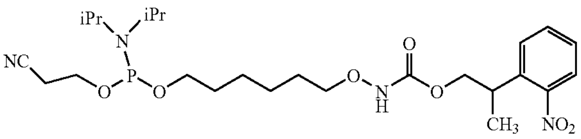

Compound (5) obtained above in the preceding step (0.90 g; 2.7 mmol) was solubilized under a stream of argon in 15 ml of dichloromethane and then diisopropyl-ethylamine (DIEA) (0.56 ml, 3.2 mmol) was added, followed by 0.72 ml of 2-cyanoethyldiisopropylchloro-phosphoramidite (3.2 mmol). The reaction mixture was stirred at ambient temperature for 4 hours until the starting product had disappeared. 40 ml of dichloromethane were then added and then the organic phase was washed with a saturated solution of sodium hydrogen carbonate and then with a saturated aqueous solution of NaCl. The organic phase was dried over anhydrous sodium sulfate and then evaporated. The crude product was purified by silica gel chromatography using dichloromethane and then a 97/3 (v/v) dichloromethane/methanol mixture as eluent. Compound (6) was obtained in the form of a yellow oil (0.50 g; 1.0 mmol) with a yield of 38%.

$^1$H-NMR (200 MHz, $CDCl_3$): δ ppm=1.20-1.50 (15H, m, 4 $C\underline{H}_3$), 1.50-1.85 (8H, m, 4 $C\underline{H}_2$), 2.65 (2H, t, $C\underline{H}_2$CN), 3.80 (2H, m, $C\underline{H}_2$OH, 1H, m, C$\underline{H}$, 4H, m, 2 $C\underline{H}_2$OP), 4.30 (2H, m, $C\underline{H}_2$OCO, 2H, m, 2 C$\underline{H}$N, 7.10-7.70 (4H Ar—$\underline{H}$ NPPOC).

$^{31}$P-NMR (200 MHz, $CDCl_3$): δ ppm 120 (2 diastereoisomers).

Example 2

Preparation of an Active Ester Derivative in Accordance with Formula (I) (Compound (8))

(8)

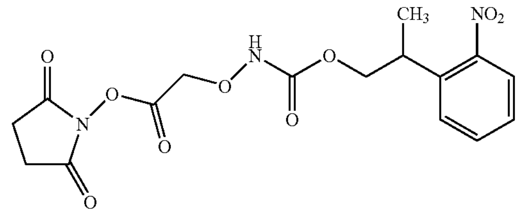

1) First Step: Preparation of the Precursor Acid (7)

(7)

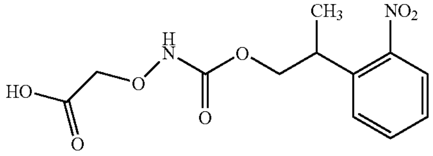

Carboxymethoxylamine hydrochloride (1 g; 4.57 mmol) was dissolved in 25 ml of a 10% aqueous solution of sodium carbonate. The solution were cooled to a temperature of 0° C. and 20 ml of a solution of dioxane containing 2.20 g (9.1 mmol) of 2-(2-nitrophenyl)propyl chloroformate (Cl—NP-POC) were added dropwise under stirring. The stirring was maintained for 2 to 3 hours at ambient temperature. The reaction medium was evaporated to dryness. 250 ml of water were added to the residue thus obtained and then the aqueous phase was washed with 200 ml of diethyl ether. The aqueous phase was then acidified with a 1N hydrochloric acid solution, to pH 3, and extracted with three times 250 ml of dichloromethane. The organic phases were combined and dried over anhydrous sodium sulfate. The crude product was purified by silica gel chromatography using dichloromethane and then a 97/3 (v/v) dichloromethane/methanol mixture as eluent. Compound (7) was obtained in the form of a white powder that melts at between 88 and 92° C. (1.20 g; 4.0 mmol), with a yield of 90%.

$^{1}$H-NMR (200 MHz, $CDCl_3$): δ ppm =1.40 (3H, d, J=16 Hz, $C\underline{H}_3$), 3.70 (1H, m, $C\underline{H}$), 4.30 (2H, m, $C\underline{H}_2O$) 4.40 (s, 2H, $COC\underline{H}_2O$), 7.30-7.60 (4H, m, Ar—$\underline{H}$ NPPOC).

$^{13}$C-NMR (300 MHz, $CDCl_3$): δ ppm=18 ($\underline{C}H_2$), 33 ($\underline{C}H_2$), 67 ($\underline{C}H_3$), 70 ($\underline{C}H_3$), 75 ($\underline{C}H_3$), 123 (quat), 137 (quat), 138 (quat), 133 (quat), 136 ($\underline{C}H$), 151 ($\underline{C}H$), 159 ($\underline{C}H$), 172 ($\underline{C}H$), 173 ($\underline{C}H$).

MS (ESI, positive mode): $M_{calc}$=298 ($C_{12}H_{14}N_2O_7$), m/z=321 $[M+Na]^+$, m/z=337 $[M+K]^+$.

MS (ESI, negative mode): m/z=297 $[M-H]^-$, m/z=595 $[2M-H]^-$.

2) Second Step: Preparation of the N-hydroxysuccinimide Activated Ester (8)

(8)

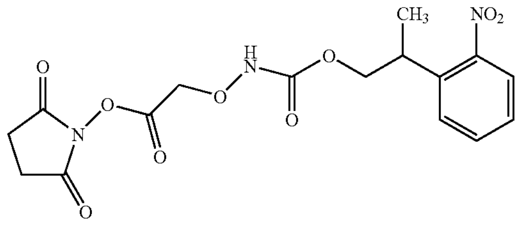

The acid (7) obtained above in the preceding step (1.20 g; 4.0 mmol) was dissolved in 15 ml of anhydrous dichloromethane and then dicyclocarbodiimide (DCC) (0.82 g; 4.4 mmol) was added, followed by N-hydroxysuccinimide (0.457 g; 4.4 mmol). The reaction medium was stirred overnight. After filtration, the solvent was evaporated off under reduced pressure. The crude product was purified by rapid silica gel chromatography using ethyl acetate as eluent. Compound (8) was obtained in the form of a yellow powder (1.0 g; 2.68 mmol) with a yield of 67%.

Example 3

Preparation of an Ester Derivative of Formula (I) Activated with Pentafluorophenol (9)

(9)

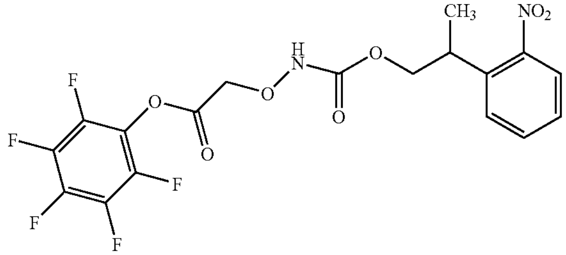

500 mg (1.6 mmol) of compound (7) obtained in the first step of example 2 above were dissolved in 5 ml of dichloromethane and then 372 mg (1.9 mmol) of pentafluorophenol were added, followed, dropwise, by 1 ml of a solution of DCC (360 mg, 1.9 mmol) in dichloromethane. The mixture was stirred for 4 hours, and then the dicyclourea (DCU) precipitate formed was filtered off. After evaporation of the solvent, compound (9) was obtained in the form of an oil (740 mg, 1.9 mmol), with a yield of 100%.

$^{1}$H-NMR (200 MHz, $CDCl_3$): δ ppm=1.30 (3H, d, J=16 Hz, $C\underline{H}_3$, 3.70 (1H, m, $C\underline{H}$), 4.30 (2H, m, $C\underline{H}_2O$), 4.70 (s, 2H, $COC\underline{H}_2O$), 7.30-7.70, (4H, m, Ar—$\underline{H}$ NPPOC).

$^{19}$F-NMR (200 MHz, $CDCl_3$): δ ppm=−166.0 (1F, t), −164.0 (1F, d), −162.0 (1F, t), −157.0 (1F, t), −152.50 (1F, d).

Example 4

Preparation of a Triethoxysilane Derivative of Formula (I)

(11)

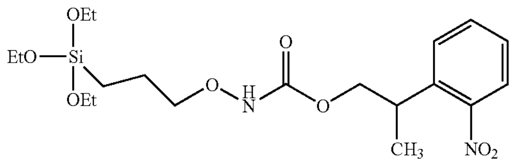

1) First Step: Preparation of N-nitrophenyl-propyloxycarbonylallyloxyamine (10)

(10)

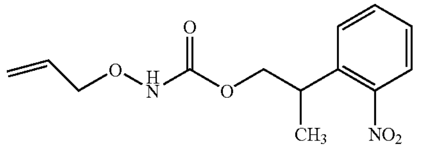

15 ml of a solution of dichloromethane containing 6 g (27 mmol) of 2-(2-nitrophenyl)propyl chloroformate (Cl—NP- POC) were added, dropwise, to a solution of 3.250 g (29.6 mmol; 1.1 equivalents) of commercial allyloxyamine in 25 ml of anhydrous pyridine cooled to a temperature of 0° C. After stirring for 30 minutes, the solvent was evaporated off and then coevaporated with toluene. The reaction crude product was dissolved in ethyl acetate. The organic phase was washed, dried over anhydrous sodium sulfate, and then evaporated at reduced pressure. Compound (10) was obtained after purification by silica gel chromatography using a mixture of ethyl acetate/hexane: 1/4 (v/v) as eluent, with a yield of 72% (5.76 g).

$^1$H-NMR (200 MHz, $CDCl_3$): δ ppm=1.40 (d, 6H, Si—$CH_2$—$C\underline{H}_3$), 3.70 (q, 1H, Ar—CH—$CH_3$), 4.30 (m, 4H, $C\underline{H}_2O$, $OC\underline{H}_2$), 5.30 (dd, 2H, $C\underline{H}_2$), 5.90 (m, 1H, $C\underline{H}$), 7.20 (s, 1H, NH), 7.30-7.80 (m, 4H, $\underline{H}$—Ar).

2) Second Step: Hydrosilylation so as to Produce Compound (11)

20 μl of Karsted catalyst were added, dropwise, to a solution of 1.67 g (5.6 mmol) of compound (10) obtained above in the preceding step in 8 ml of triethoxysilane. After stirring overnight at a temperature of 60° C., the solvent was evaporated off by distillation under vacuum. The reaction crude product was purified by silica gel chromatography using a 1/4 (v/v) ethyl acetate/hexane mixture as eluent, so as to produce the expected compound (11) with a yield of 60% (1.33 g).

$^1$H-NMR (200 MHz, $CDCl_3$): δ ppm=0.65 (m, 2H, $C\underline{H}_2Si$), 1.20 (t, 3H, $C\underline{H}_3$—$CH_2$—O), 1.40 (d, 3H, $C\underline{H}_3$—CH), 1.70 (m, 3H, $C\underline{H}_2$, $C\underline{H}$—$CH_3$), 3.80 (m, 4H, O—$C\underline{H}_2$—$CH_3$, $C\underline{H}_2O$), 4.30 (m, 2H, $C\underline{H}_2$—O—CO), 7.30-7.80 (m, 5H, $N\underline{H}$, $\underline{H}$—Ar).

MS (electrospray, positive mode): $M_{calc}$=444, m/e=44.7 $[M+H]^+$.

The examples of preparation of solid supports which follow were carried out with the coupling agents of formula (I) in accordance with the invention, in capillary tube format (glass capillary tubes 3 cm in length and 100 μm in diameter). It should be clearly understood, however, that these examples are transposable to a planar format on other types of support.

Example 5

Preparation of a Solid Support Functionalized with a Coupling Agent of Formula (I) Comprising an Attachment Function A of Silane Type In this example, compound (11) as prepared above in example 4 was used as coupling agent of formula (I).

A solid support functionalized by compound (11) is obtained in a single step, in this case by means of the step referred to as silanization of the surface of the mineral solid support (glass capillary tube) according to the reaction scheme below:

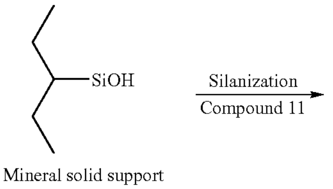

Mineral solid support

-continued

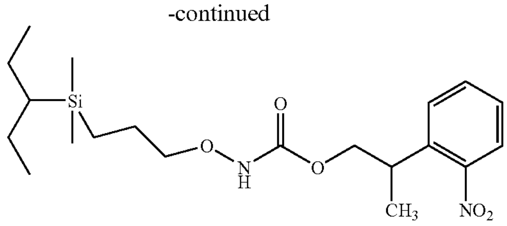

Photosensitive oxyamine surface

To do this, a capillary tube was filled with a 6M solution of sodium hydroxide in a 1/1 water/ethanol mixture and the solution was left in the capillary tube for 2 hours at ambient temperature.

The capillary tube was subsequently thoroughly rinsed with water and was then dried with nitrogen.

The capillary tube was subsequently filled with a solution of compound (11) at 10 mM in trichloroethylene and this was left to act overnight at ambient temperature.

The capillary tube was subsequently thoroughly rinsed with trichloroethylene, absolute ethanol and then chloroform and, finally, dried with nitrogen.

A glass capillary tube, the inner surface of which was functionalized with a layer of compound (11), i.e. a photosensitive oxyamine surface, was thus obtained.

Example 6

Preparation of a Solid Support Functionalized with a Coupling Agent of Formula (I) Comprising an Attachment Function A of Activated Ester Type In this example, compound (8) as prepared above in example 2, comprising an attachment function A of NHS-activated ester type, was used as coupling agent of formula (I).

A solid support functionalized with this NHS-activated ester coupling agent is obtained in two steps, according to the reaction scheme below:

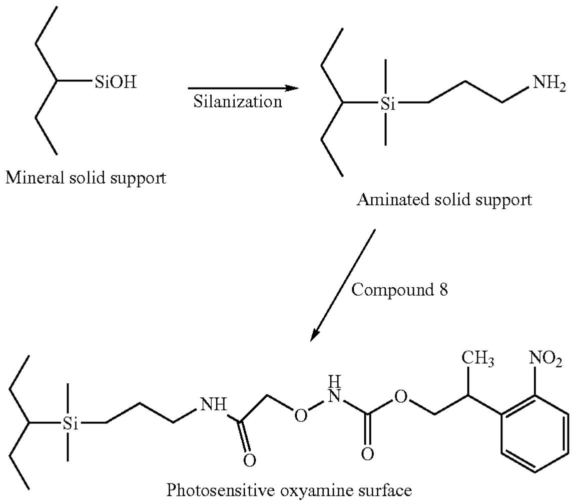

Photosensitive oxyamine surface

According to which, in a first step, the mineral surface of the solid support is converted to a surface comprising amine functions and, in a second step, said surface amine functions are reacted with compound (8).

1) First Step: Preparation of a Surface Comprising Amine Functions

A glass capillary tube was filled with a 6M solution of sodium hydroxide in a 1/1 water/ethanol mixture and the solution was left in the capillary tube for 2 hours at ambient temperature.

The capillary tube was rinsed thoroughly with water and was then dried with nitrogen.

The capillary tube was subsequently filled with a solution of triethoxyaminopropylsilane at 10% in 95° ethanol and the solution was left in the capillary tube overnight at ambient temperature. The capillary tube was subsequently rinsed with ethanol and then dried with nitrogen.

A capillary tube, the inner surface of which was covered with amine functions, was obtained.

2) Second Step: Functionalization of the Support with Compound (8)

The capillary tube obtained above in the first step was filled with a solution of compound (8) at 10 mM in dimethylformamide (DMF) and the solution was left in the capillary tube overnight at ambient temperature.

The capillary tube was subsequently rinsed with DMF and then with ethanol and, finally, dried with nitrogen.

A glass capillary tube, the inner surface of which was functionalized with a layer of compound (8), i.e. a photosensitive oxyamine surface, was thus obtained.

Example 7

Use of a Functionalized Support for the Immonilization of Biological Molecules of Interest In this example, the solid support obtained above in example 5 was used for the immobilization of oligonucleotides (ONs). It should be clearly understood, however, that the use of these supports for the immobilization of other biological molecules of interest is also valid.

In the case of the oligonucleotides, the grafting of these molecules and the demonstration of their presence on the surface of the solid support are composed of four steps:

(i) exposure: this is the step which makes it possible to locally free the reactive function B on the surface of the solid support under the action of light. This function B will allow the grafting of the biomolecule.

(ii) immobilization: this is the step of grafting, per se, of the ON by means of the reaction between the aldehyde function carried by the ON and the photo-deprotected function B at the surface of the solid support after the exposure step.

(iii) hybridization: this is the step of demonstration of the possible grafting of the desired ON by means of the recognition of the ON grafted onto the surface of the solid support by its complementary sequence carrying a fluorophore.

(iv) detection of the fluorescence with a scanner: this is the step of the processing of any signal emitted by the fluorophore.

I) Procedure:

1) Exposure Step

The capillary tube functionalized with compound (11) as prepared above in example 5 was filled with a 1/1 pyridine/water mixture.

An exposure of the capillary tube was subsequently carried out at various chosen sites of said tube for 5 seconds, using an ultraviolet A (UVA) radiation exposing device at a wavelength of 365 nm, adjusting the slot size to 160 μm, with an intensity of 4 $mW/mm^2$, said exposing device being equipped with a 100 W lamp.

The capillary tube was subsequently rinsed with water and then dried with nitrogen.

2) ON Immobilization Step

The capillary tube thus treated according to the first step was incubated with a solution of ONs carrying an aldehyde function, at 10 μM in water, and the whole was left to act for 30 minutes.

The capillary tube was subsequently rinsed with water, then with a 0.2% solution of sodium lauryl sulfate, and then again with water and, finally, dried with nitrogen.

3) Hybridization Step

The capillary tube on which the ONs were immobilized in accordance with step 2) above was filled with a solution of complementary ONs carrying the CY3 fluorophore and the whole was left to act for 1 hour at a temperature of 40° C.

The capillary tube was subsequently rinsed with a 0.2% solution of sodium citrate.

4) Reading Step

The capillary tube on which the fluorophore-labeled ONs had hybridized in accordance with step 3) above was placed on a glass slide and then introduced into a fluorescence reader sold by the company Genomic's Solution.

The same measurement was also carried out on a control capillary tube (type b/) having been subjected to the same treatments as those described above for the test capillary tube (type a/), except for the step of functionalization with the coupling agents of formula (I).

II/Results

The image of the fluorescence obtained is represented in the attached FIG. 1, in which it may be noted that only the sites having been exposed are fluorescent. It is seen, moreover, that only the capillary tube functionalized with the coupling agents of formula (I) in accordance with the invention (type a/) comprises fluorescent segments corresponding to the photo-localized immobilization of the desired ONs, the nonfunctionalized capillary tube (type b/) being completely nonfluorescent.

This example demonstrates that the solid supports in accordance with the invention can be advantageously used for the immobilization of molecules of interest in a specific and localized manner.

Example 8

Preparation of a Triethoxysilane Derivative of Formula (I) (15)

(15)

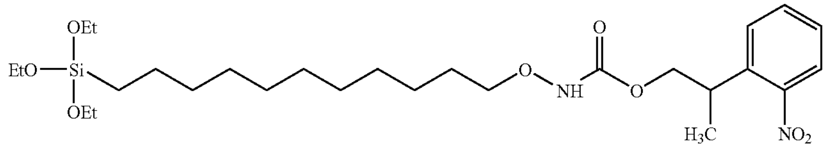

1) First Step: Preparation of a Compound (12): Introduction of the Oxyamine (12)

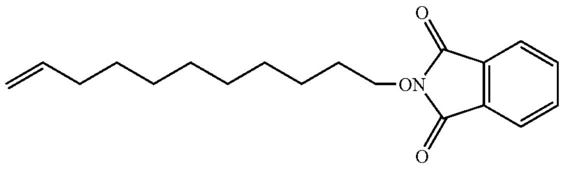

A solution of N-hydroxyphthalimide (3.50 g; 21 mmol) and of potassium carbonate (8 g; 41 mmol) in 250 ml of dimethylformamide (DMF) was heated at a temperature of 50° C. under argon for one hour with stirring. 11-Bromo-undecene (5.0 g; 21 mmol) was subsequently added and then the reaction mixture was again stirred for 3 hours at a temperature of 50° C. After filtration, the solvent was evaporated off under reduced pressure. 100 ml of dichloromethane were subsequently added to the residue thus obtained and then the organic phase was washed with 0.1 N sodium hydroxide and then with a saturated aqueous solution of sodium chloride. The organic phase was subsequently dried over anhydrous sodium sulfate and then evaporated. The product (12) was obtained in the form of a white powder (6.45 g; 20.4 mmol; yield 97%) having a melting point of between 38 and 40° C.

The proton nuclear magnetic resonance ($^1$H-NMR) analysis, carried out at a wavelength of 200 MHz in $CDCl_3$, was as follows:

δ ppm=1.20-1.50 (12H, m, 6 $C\underline{H}_2$); 1.78 (2H, m, J=7 Hz, $C_2\underline{H}_3CH_2C\underline{H}2CH_2$); 2.02 (2H, m, $C_2\underline{H}_3C\underline{H}_2CH_2$); 4.18 (2H, t, J=6 Hz, $C\underline{H}_2ON$); 4.95 (2H, m, $C\underline{H}_2CHCH_2$); 5.79 (1H, m, $CH_2C\underline{H}CH_2$); 7.70-7.85 (4H, m, Ar—$\underline{H}$).

MS (ESI, positive mode): $M_{calc}$–315 ($C_{19}H_{25}NO_3$), m/z=338 $[M+Na]^+$.

2) Second Step: Hydrazinolysis of Compound (12) so as to Produce Compound (13)

(13)

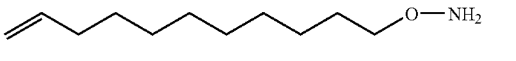

Compound (12) (3.0 g; 9.64 mmol) obtained above in the first step was solubilized in 30 ml of dichloromethane and 966 mg of hydrazine (19.3 mmol) were added. The solution obtained was brought to reflux for 3 hours and then filtered and evaporated under reduced pressure. The crude product was purified by silica gel chromatography, with a mixture of ethyl acetate and cyclohexane (v/v: 1/2) as eluent. Compound (13) was obtained in the form of a translucent oil (1.65 g; 8.94 mmol) with a yield of 93%.

$^1$H-NMR (200 MHz, $CDCl_3$): δ ppm=1.20-1.50 (12H, m, 4 $C\underline{H}_2$), 1.56 (2H, m, $C_2\underline{H}_3CH_2C\underline{H}_2CH_2$), 2.03 (2H, q, $C_2\underline{H}_3C\underline{H}_2CH_2$), 3.65 (2H, t, J=6 Hz, $C\underline{H}_2ON$), 4.96 (2H, m, $C\underline{H}_2CHCH_2$), 5.80 (1H, m, $CH_2C\underline{H}CH_2$).

MS (ESI, positive mode): $M_{calc}$=185 ($C_{11}H_{23}NO$), m/z=186 $[M+H]^+$.

3) Third Step: Protection of the Oxyamine of Compound (13) so as to Obtain Compound (14)

(14)

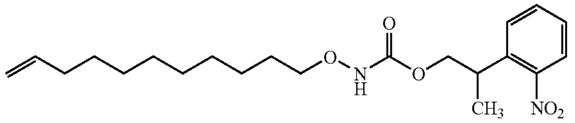

Compound (13) prepared above in the second step (470 mg; 2.54 mmol) was dissolved in 2 ml of pyridine. 3 ml of a solution of dichloromethane containing 620 mg (5.08 mmol) of 2-(2-nitrophenyl)propyl chloroformate (Cl—NPPOC) were subsequently added dropwise. The reaction mixture was stirred for 2 hours in the dark and then filtered and evaporated under reduced pressure. The residue obtained was subsequently solubilized in dichloromethane and then the organic phase was washed with a 10% (w/v) aqueous solution of sodium carbonate, then with an aqueous solution of hydrochloric acid (1N) and, finally, with a saturated aqueous solution of sodium chloride. The organic phase was dried over anhydrous sodium sulfate and then evaporated. The crude product was purified by silica gel chromatography using a mixture of ethyl acetate and cyclohexane (v/v: 1/4) as eluent. The product (14) was obtained in the form of an orange oil (873 mg; 2.22 mmol) with a yield of 88%.

$^1$H-NMR (200 MHz, $CDCl_3$): δ ppm=1.20-1.40 (12H, m, 6 $C\underline{H}_2$), 1.35 (3H, d, J=7 Hz, $C\underline{H}_3$), 1.56 (2H, m $C_3H_3CH_2C\underline{H}2CH_2$), 2.03 (2H, m, $C_2H_3C\underline{H}_2CH_2$), 3.65 (2H, m, $C\underline{H}_2ON$, 1H, m, $C\underline{H}$), 4.28 (2H, m, $C\underline{H}_2OCO$), 4.96 (2H, m, $C\underline{H}_2CHCH_2$), 5.80 (1H, m, $CH_2C\underline{H}CH_2$), 7.20-7.80 (4H, m, Ar—$\underline{H}$ NPPOC).

MS (ESI, positive mode):$M_{calc}$=392 ($C_{21}H_{32}N_2O_5$), m/z=415 $[M+Na]^+$, m/z=410 $[M+NH_4]^+$.

4) Fourth Step: Hydrosilylation of Compound (14) so as to Obtain Compound (15)

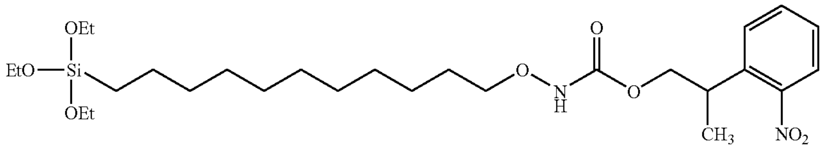

(15)

1.28 g (3.2 mmol) of compound (14) obtained according to the process described above in step 3 were added to a solution consisting of 5 ml of triethoxysilane and 14 μl (0.25 equivalent) of Karsted catalyst. The reaction mixture was stirred for 2 hours at a temperature of 60° C. and then the solvent was evaporated off and coevaporated with DMF (5 to 6 times) under vacuum. The expected product (15) was obtained in the form of an oil (1.49 g; 2.68 mmol) with a yield of 83%.

$^1$H-NMR (200 MHz, $CDCl_3$): δ ppm=0.6 (2H, m, C$\underline{H}_2$Si), 1.20-1.40 (16H, m, 6 C$\underline{H}_2$, 9H 3 $CH_3CH_2OSi$), 1.35 (3H, d, J=7 Hz, C$\underline{H}_3$), 3.65 (2H, m, $\underline{C}H_2ON$, 1H, m, C$\underline{H}$), 4.28 (2H, m, $\underline{C}H_2OCO$), 7.20-7.80 (4H, m, Ar—$\underline{H}$ NPPOC).

MS (ESI, positive mode): $M_{calc}$=556 ($C_{27}H_{48}N_2O_8$ Si), m/z=579 $[M+Na]^+$.

Example 9

Preparation of a Planar Solid Support Functionalized with a Coupling Agent of Formula (I) Comprising an Attachment Function A of Silane Type In this example, compound (15) as prepared above in example 8 was used as coupling agent of formula (I).

1) First Step: Rehydration of the Surface (Activation)

A solid planar silicon support comprising inactive $SiO_2$ functions was immersed in a solution consisting of 4 ml of water and 3 ml of ethanol and containing sodium hydroxide (1 g NaOH), for 1 hour. The support was subsequently rinsed with ultrapure water, then with a 0.2 N solution of hydrochloric acid and, finally, with water, which produced a surface comprising activated SiOH functions. The support was subsequently dried with argon.

2) Second Step: Silanization of the Support with Compound (15)

The support thus activated was soaked in a solution of compound (15) (7 ml) at 5 mM in a toluene/triethylamine (v/v: 97/3) mixture overnight at 80° C. The support was subsequently washed with toluene and then with ethanol and, finally, dried with argon. The support thus functionalized with compound (15) was subsequently placed in an incubator at 110° C. for 3 hours.

Example 10

Use of a Solid Planar Support Functionalized with a Compound of Formula (I) for the Immobilization of Biological Molecules of Interest Just as described above in example 7, the ON grafting and the demonstration of their presence at the surface of the solid support are composed of four steps: exposure, immobilization, hybridization and, finally, detection of the fluorescence with a scanner.

I) Procedure:

1) First Step: Exposure of the Support

The solid planar support, functionalized with compound (15) according to the process described above in example 9, onto which has been applied a plastic mask which comprises transparent spots 100 μm by 100 μm in size which allow light to pass through, was covered with a drop of a 1/1 (v/v) mixture of pyridine/water. An exposure over the entire surface of the support, and therefore through the mask, was then carried out for 15 seconds using an ultraviolet A (UVA) radiation exposing device at a wavelength of 365 nm, with an intensity of 4 mW/mm$^2$, said exposing device being equipped with a 100 W lamp.

The solid planar support was then rinsed with water and then dried with nitrogen.

2) Second Step: ON Immobilization

The planar support thus treated according to the first step was incubated with a solution of ON carrying an aldehyde function, at 10 μM in water, and the whole was left to act for 30 minutes.

The support was then rinsed with water, then with a 0.2% solution of sodium lauryl sulfate and then again with water and, finally, dried with nitrogen.

3) Third Step: Hybridization

The solid support on which the ONs were immobilized in accordance with step 2) above was filled with a solution of complementary ONs carrying the CY3 fluorophore and the whole was left to act for 1 hour at a temperature of 40° C. The support was then rinsed with a 0.2% solution of sodium citrate.

4) Fourth Step: Reading

The support on which the fluorophore-labeled ONs had hybridized in accordance with step 3) above was placed on a glass slide and then introduced into a fluorescence reader sold by the company Genomic's Solution.

The same measurement was also carried out on a control solid planar support (type b/) having been subjected to the same treatments as those described above for the test capillary tube (type b/), except for the step of functionalization with compound (15).

Figure 2:
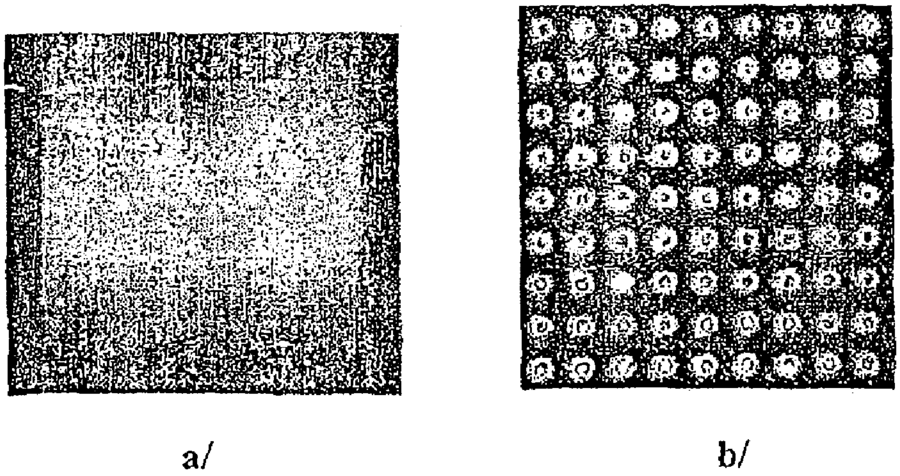
FIG. 2 represents the photograph of the fluorescence emitted by oligonucleotides attached to a planar solid support according to the process in accordance with the invention, after hybridization with complementary oligonucleotides labeled with a fluorophore (support of type a/), compared with a nonfunctionalized support (support of type b/).

II) Results:

The image of the fluorescence obtained is represented in the attached FIG. 2, in which it can be noted that only the sites having been exposed are fluorescent. It is seen, moreover, that only the solid planar support functionalized with the coupling agents (15) in accordance with the invention (support of type a/) comprises fluorescent spots corresponding to the photo-localized immobilization of the desired ONs, the nonfunctionalized support (support of type b/) being completely non-fluorescent.

This example demonstrates that the solid supports in accordance with the invention can be advantageously used for the immobilization of molecules of interest in a specific and localized manner.

What is claimed is:

1. A coupling agent of formula (I) below:

A—X—B—Proc (I)

in which:

A represents a function for attachment to a solid support, said function being chosen from functions of amine, phosphoramidite, silane and activated ester type;

X represents a spacer arm;

B is a reactive function chosen from groups that result, after photodeprotection, in a function of the type oxyamine (—$ONH_2$) and derivatives or hydrazide (—NH—$NH_2$) and derivatives, said function B being protected with a Proc group;

Proc is a photolabile protecting group of formula (II) below:

(II)

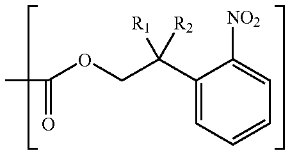

in which:

$R_1$ and $R_2$, which may be identical or different, represent a hydrogen atom or a $C_1$-$C_4$ alkyl radical.

2. The coupling agent as claimed in claim 1, characterized in that the spacer arm X is an uncharged hydrophobic chain or an uncharged hydrophilic chain.

3. The coupling agent as claimed in claim 2, characterized in that the spacer arm X is chosen from saturated hydrocarbon-based chains containing from 1 to 13 carbon atoms, and glycol ethers in which the carbon-based chain contains from 4 to 12 carbon atoms.

4. The coupling agent as claimed in claim 1, characterized in that $R_1$ and $R_2$, independently of one another, represent an alkyl radical chosen from methyl and ethyl radicals.

5. The coupling agent as claimed in claim 1, characterized in that it is chosen from those in which:

i) A represents a phosphoramidite function,

X represents a saturated hydrocarbon-based chain having 6 carbon atoms,

B represents an oxyamine function (—ONH—), and $R_1$ and $R_2$ represent a hydrogen atom or a methyl radical;

ii) A represents a tri($C_1$-$C_4$) alkoxysilane,

X represents a saturated hydrocarbon-based chain having from 2 to 12 carbon atoms, B represents an oxyamine function (—ONH—), and $R_1$ and $R_2$ represent a hydrogen atom or a methyl radical;

iii) A represents a carboxylic function esterified with N-hydroxysuccinimide, or pentafluorobenzene, X represents —$CH_2$—, B represents an oxyamine function (—ONH—), and $R_1$ and $R_2$ represent a hydrogen atom or a methyl radical.

6. The coupling agent as claimed in claim 5, characterized in that the compounds ii) are chosen from compounds in which the function A is triethoxysilane and X is a saturated hydrocarbon-based chain having 3 or 11 carbon atoms.

7. A method for the functionalization of sold supports comprising the steps of using at least one coupling agent of formula (I) below:

A—X—B—Proc (I)

in which:

A represents a function for attachment to a solid support, said function being chosen from functions of amine, phosphoramidite, silane and activated ester type;

X represents a spacer arm;

B is a reactive function chosen from groups that result, after photodeprotection, in a function of the type oxyamine (—$ONH_2$) and derivatives or hydrazide (—NH—$NH_2$) and derivatives, said function B being protected with a Proc group;

Proc is a photolabile protecting group of formula (II) below:

(II)

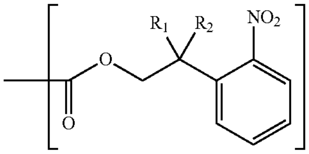

in which:

$R_1$ and $R_2$, which may be identical or different, represent a hydrogen atom or a $C_1$-$C_4$ alkyl radical.

8. A process for preparing a functionalized solid support, characterized in that it comprises at least one step of bringing at least one surface of a solid support into contact with a solution, in an organic solvent, of at least one coupling agent of formula (I) as defined in claim 1.

9. The process as claimed in claim 8, characterized in that the bringing into contact of the solid support with the solution of coupling agent of formula (I) is carried out at a temperature of between 4 and 80° C. for 1 to 48 hours.

10. The process as claimed in claim 8, characterized in that the solid support is chosen from supports made of glass, ceramics, silicon or plastic, said supports comprising at least one hydrated, hydroxylated, silanized or aminated surface or a surface of activated ester type.

11. The process as claimed in claim 8, characterized in that the support has at least one planar or nonplanar, smooth or structured surface, and is in the form of a glass slide, a planar plastic plate or a plastic plate with wells, a capillary tube or a porous or nonporous bead.

12. A solid support characterized in that it comprises at least one surface functionalized with one or more coupling agents of formula (I) as defined in claim 1.

13. A process for immobilizing biological molecules of interest on a solid support, the solid support comprising at least one surface functionalized with one or more coupling agents of formula (I) below:

A—X—B—Proc (I)

in which:

A represents a function for attachment to a solid support, said function being chosen from functions of amine, phosphoramidite, silane and activated ester type;

X represents a spacer arm;

B is a reactive function chosen from groups that result, after photodeprotection, in a function of the type oxyamine (—$ONH_2$) and derivatives or hydrazide (—NH—$NH_2$) and derivatives, said function B being protected with a Proc group;

Proc is a photolabile protecting group of formula (II) below:

(II)

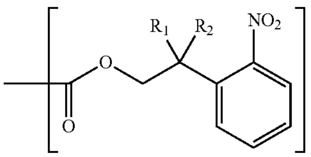

in which:

$R_1$ and $R_2$, which may be identical or different, represent a hydrogen atom or a $C_1$-$C_4$ alkyl radical characterized in that it comprises at least a first step of photo-deprotection of the reactive functions B of the compounds of formula (I) by exposure of at least a part of the surface of the solid support, followed by bringing the solid support thus activated into contact with a solution of biological molecules of interest, so as to result in the immobilization of said molecules through the formation of a covalent bond between at least one chemical function that is carried by said molecules and that is reactive with respect to the reactive functions B of said compounds of formula (I), on said solid support, and the optional repetition of these two steps.

14. The process as claimed in claim 13, characterized in that the photo-deprotection step is localized on only a part of the functionalized surface of the solid support.

15. The process as claimed in claim 13, characterized in that the immobilization step is carried out through the formation of oxime bonds between the oxyamine functions B of the compounds of formula (I) and carbonylated functions of the biological molecules of interest.

16. The process as claimed in claim 15, characterized in that the immobilization step is carried out at a pH of between 4 and 7.

17. The process as claimed in claim 14, characterized in that the exposure wavelength is between 300 and 400 nm.

* * * * *